(12) United States Patent
Faries, Jr. et al.

(10) Patent No.: US 7,540,864 B2
(45) Date of Patent: Jun. 2, 2009

(54) TEMPERATURE SENSING DEVICE FOR SELECTIVELY MEASURING TEMPERATURE AT DESIRED LOCATIONS ALONG AN INTRAVENOUS FLUID LINE

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Medical Solutions, Inc., Chantilly, VA (US)

( * ) Notice: Subject to any disclaimer, the term of this patent is extended or adjusted under 35 U.S.C. 154(b) by 551 days.

(21) Appl. No.: 10/849,251

(22) Filed: May 20, 2004

(65) Prior Publication Data

US 2004/0249336 A1 Dec. 9, 2004

Related U.S. Application Data

(60) Division of application No. 09/973,988, filed on Oct. 11, 2001, now Pat. No. 7,090,658, which is a continuation-in-part of application No. 09/380,507, filed as application No. PCT/US98/04199 on Mar. 3, 1998, now Pat. No. 6,824,528.

(60) Provisional application No. 60/040,885, filed on Mar. 3, 1997, provisional application No. 60/062,315, filed on Oct. 17, 1997.

(51) Int. Cl.
*A61M 31/00* (2006.01)
*A61F 7/12* (2006.01)
*G01K 1/08* (2006.01)

(52) U.S. Cl. .................. 604/500; 604/113; 374/147

(58) Field of Classification Search ......... 604/113–114, 604/500, 506; 374/208, 147–148; 285/93
See application file for complete search history.

(56) References Cited

U.S. PATENT DOCUMENTS 522,866 A 7/1894 Weinhagen et al.

(Continued)

FOREIGN PATENT DOCUMENTS

DE 37 09 122 A1 9/1988

(Continued)

OTHER PUBLICATIONS

*Health Devices*, vol. 25, No. 10, Oct. 1996.

(Continued)

*Primary Examiner*—Mark W Bockelman
(74) *Attorney, Agent, or Firm*—Edell, Shapiro & Finnan, LLC

(57) ABSTRACT

A temperature sensing device measures the temperature of a fluid at selected locations along an IV fluid line. The device is secured to a selected portion of the IV line and includes a temperature sensor for measuring fluid flowing within that line. The device is coupled to a temperature display device to display the measured temperature. The temperature sensing device may include: a housing with a lower cover to engage the line and a temperature sensor; a holder movable along the line and including a temperature sensor; a housing with a lower member including a tip to pierce and measure temperature of fluid within the line; a resilient member with a spiral configuration and a tip to pierce and measure temperature of fluid within the line; a 'T'-type fitting including a temperature sensor; or a 'Y'-type fitting including a temperature sensor in the form of a needle.

16 Claims, 7 Drawing Sheets

U.S. PATENT DOCUMENTS

| | | |
|---|---|---|
| 558,979 A | 4/1896 | Noble |
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,204,764 A | 6/1940 | Mayo |
| 2,254,994 A | 9/1941 | Butland |
| 2,470,481 A | 5/1949 | Freeman |
| 2,701,789 A | 2/1955 | White |
| 2,766,907 A | 10/1956 | Wallace, Jr. |
| 2,910,981 A | 11/1959 | Wilson et al. |
| 3,140,716 A | 7/1964 | Harrison et al. |
| 3,247,851 A | 4/1966 | Seibert |
| 3,293,868 A | 12/1966 | Gonzalez |
| 3,370,153 A | 2/1968 | Du Fresne et al. |
| 3,475,590 A | 10/1969 | Pins |
| 3,485,245 A | 12/1969 | Lahr et al. |
| 3,526,134 A | 9/1970 | Schaus |
| 3,551,641 A | 12/1970 | Truhan |
| 3,590,215 A | 6/1971 | Anderson et al. |
| 3,612,059 A | 10/1971 | Ersek |
| 3,614,385 A | 10/1971 | Horstmann |
| 3,629,552 A | 12/1971 | Edging |
| 3,636,767 A | 1/1972 | Duffy |
| 3,640,277 A | 2/1972 | Adelberg |
| 3,651,695 A | 3/1972 | Brown |
| 3,845,661 A | 11/1974 | Hollweck et al. |
| 3,895,741 A | 7/1975 | Nugent |
| 3,908,652 A | 9/1975 | Weissinger |
| 3,940,742 A | 2/1976 | Hudspeth et al. |
| 4,009,615 A | 3/1977 | Ruhl |
| 4,038,519 A | 7/1977 | Foucras |
| 4,090,514 A | 5/1978 | Hinck et al. |
| 4,098,123 A | 7/1978 | Granzow, Jr. |
| 4,121,574 A | 10/1978 | Lester |
| 4,138,890 A | 2/1979 | Brown |
| 4,167,663 A | 9/1979 | Granzow, Jr. et al. |
| 4,187,847 A | 2/1980 | Loeser |
| 4,293,762 A | 10/1981 | Ogawa |
| 4,309,592 A | 1/1982 | Le Boeuf |
| 4,329,569 A | 5/1982 | Hjortsberg et al. |
| 4,336,435 A | 6/1982 | Kashyap et al. |
| 4,356,383 A | 10/1982 | Dahlberg |
| 4,375,813 A | 3/1983 | Hessel |
| 4,384,578 A | 5/1983 | Winkler |
| 4,430,078 A | 2/1984 | Sprague |
| 4,464,563 A | 8/1984 | Jewett |
| 4,476,877 A | 10/1984 | Barker |
| 4,490,884 A | 1/1985 | Vickers |
| 4,495,402 A | 1/1985 | Burdick et al. |
| 4,523,078 A | 6/1985 | Lehmann |
| 4,531,941 A | 7/1985 | Zasuwa |
| 4,532,414 A | 7/1985 | Shah et al. |
| 4,543,095 A | 9/1985 | Jensen |
| 4,551,136 A | 11/1985 | Mandl |
| 4,585,441 A | 4/1986 | Archibald |
| 4,586,691 A | 5/1986 | Kozlow |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,678,460 A | 7/1987 | Rosner |
| 4,680,445 A | 7/1987 | Ogawa |
| 4,682,979 A | 7/1987 | Girouard |
| 4,684,367 A | 8/1987 | Schaffer et al. |
| 4,705,505 A | 11/1987 | Fried |
| 4,707,587 A | 11/1987 | Greenblatt |
| 4,709,135 A | 11/1987 | Dietrich et al. |
| 4,735,609 A | 4/1988 | Comeau et al. |
| 4,745,248 A | 5/1988 | Hayes |
| 4,747,450 A | 5/1988 | Ikegame et al. |
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,833 A | 4/1989 | Hogan et al. |
| 4,832,689 A | 5/1989 | Mauerer et al. |
| 4,844,074 A | 7/1989 | Kurucz |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,883,117 A | 11/1989 | Dobbs et al. |
| 4,900,308 A | 2/1990 | Verkaart |
| 4,906,816 A | 3/1990 | van Leerdam |
| 4,934,336 A | 6/1990 | White |
| 4,994,021 A | 2/1991 | Smith et al. |
| 5,013,889 A | 5/1991 | Bakke |
| 5,019,047 A | 5/1991 | Kriesel |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knoopf et al. |
| 5,063,994 A | 11/1991 | Verkaart |
| 5,073,167 A | 12/1991 | Carr et al. |
| 5,075,167 A | 12/1991 | Yamauchi et al. |
| 5,081,697 A | 1/1992 | Manella |
| 5,096,822 A | 3/1992 | Rosenkrans, Jr. et al. |
| 5,097,898 A | 3/1992 | Verkaart |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,153,827 A | 10/1992 | Coutré et al. |
| 5,169,389 A | 12/1992 | Kriesel |
| 5,180,896 A | 1/1993 | Gibby et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,232,439 A | 8/1993 | Campbell et al. |
| 5,241,951 A | 9/1993 | Mason et al. |

| Patent | Date | Inventor |
|---|---|---|
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,279,558 A | 1/1994 | Kriesel |
| 5,279,598 A | 1/1994 | Sheaff |
| 5,282,264 A | 1/1994 | Reeves et al. |
| 5,290,222 A | 3/1994 | Feng et al. |
| 5,290,230 A | 3/1994 | Ainsworth et al. |
| 5,297,234 A | 3/1994 | Harms et al. |
| 5,308,335 A | 5/1994 | Ross et al. |
| 5,318,540 A | 6/1994 | Athayde et al. |
| 5,330,431 A | 7/1994 | Herskowitz |
| 5,338,157 A | 8/1994 | Blomquist |
| 5,342,313 A | 8/1994 | Campbell et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,397,875 A | 3/1995 | Bechtold, Jr. |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,417,274 A | 5/1995 | Verkaart |
| 5,420,962 A | 5/1995 | Bakke |
| 5,423,759 A | 6/1995 | Campbell |
| 5,433,704 A | 7/1995 | Ross et al. |
| 5,451,209 A | 9/1995 | Ainsworth et al. |
| 5,474,538 A | 12/1995 | Stihler et al. |
| 5,485,408 A | 1/1996 | Blomquist |
| 5,492,534 A | 2/1996 | Athayde et al. |
| 5,512,043 A | 4/1996 | Verkaart |
| 5,514,095 A | 5/1996 | Brightbill et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,584,811 A | 12/1996 | Ross et al. |
| 5,590,648 A * | 1/1997 | Mitchell et al. ............ 600/301 |
| RE35,501 E | 5/1997 | Ross et al. |
| 5,647,854 A | 7/1997 | Olsen et al. |
| 5,649,910 A | 7/1997 | Kriesel et al. |
| 5,658,250 A | 8/1997 | Blomquist et al. |
| 5,658,252 A | 8/1997 | Johnson |
| 5,662,611 A | 9/1997 | Beiser et al. |
| 5,669,877 A | 9/1997 | Blomquist |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |
| 5,707,151 A | 1/1998 | Parker et al. |
| 5,707,431 A | 1/1998 | Verkaart et al. |
| 5,713,864 A | 2/1998 | Verkaart |
| 5,720,728 A | 2/1998 | Ford |
| 5,729,653 A | 3/1998 | Magliochetti et al. |
| 5,733,263 A | 3/1998 | Wheatman |
| 5,743,878 A | 4/1998 | Ross et al. |
| 5,755,275 A | 5/1998 | Rose et al. |
| 5,772,409 A | 6/1998 | Johnson |
| 5,788,669 A | 8/1998 | Peterson |
| 5,788,671 A | 8/1998 | Johnson |
| 5,806,528 A | 9/1998 | Magliochetti |
| 5,807,332 A | 9/1998 | Augustine et al. |
| 5,810,771 A | 9/1998 | Blomquist |
| 5,823,746 A | 10/1998 | Johnson |
| 5,824,000 A | 10/1998 | Pavlo et al. |
| 5,829,880 A | 11/1998 | Diedrich |
| 5,840,068 A | 11/1998 | Cartledge |
| 5,875,282 A | 2/1999 | Jordan |
| 5,876,370 A | 3/1999 | Blomquist |
| 5,879,143 A | 3/1999 | Cote et al. |
| 5,879,329 A | 3/1999 | Ginsburg |
| 5,891,096 A | 4/1999 | Hyun et al. |
| 5,893,843 A | 4/1999 | Rodrigues |
| 5,919,218 A | 7/1999 | Carr |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,700 A | 9/1999 | Kovelman |
| 5,961,492 A | 10/1999 | Kriesel et al. |
| 5,961,700 A | 10/1999 | Oliver |
| 5,989,238 A | 11/1999 | Ginsburg |
| 6,024,539 A | 2/2000 | Blomquist |
| 6,035,102 A | 3/2000 | Bakke |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,129,702 A | 10/2000 | Woias et al. |
| 6,139,528 A | 10/2000 | Kistner et al. |
| 6,142,974 A | 11/2000 | Kristher et al. |
| 6,146,359 A | 11/2000 | Carr et al. |
| 6,174,300 B1 | 1/2001 | Kriesel et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,236,809 B1 | 5/2001 | Cassidy et al. |
| 6,248,077 B1 | 6/2001 | Elson et al. |
| 6,254,572 B1 | 7/2001 | Knipfer et al. |
| 6,261,261 B1 | 7/2001 | Gordon |
| 6,316,750 B1 | 11/2001 | Levin |
| 6,334,707 B1 | 1/2002 | Ku |
| 6,371,121 B1 | 4/2002 | Faries, Jr. et al. |
| 6,464,666 B1 | 10/2002 | Augustine |
| 6,467,953 B1 | 10/2002 | Faries, Jr. et al. |
| 6,480,257 B2 | 11/2002 | Cassidy et al. |
| 6,524,239 B1 | 2/2003 | Reed et al. |
| 6,553,336 B1 | 4/2003 | Johnson et al. |
| 6,566,631 B2 | 5/2003 | Faries, Jr. et al. |
| 6,649,040 B1 | 11/2003 | Mirchi et al. |
| 6,660,974 B2 | 12/2003 | Faries, Jr. et al. |
| 6,722,782 B2 | 4/2004 | Faries, Jr. et al. |
| 6,736,788 B1 | 5/2004 | Mongomery et al. |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,788,885 B2 | 9/2004 | Mitsunaga |
| 6,824,528 B1 | 11/2004 | Faries, Jr. et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 7,238,171 B2 | 7/2007 | Faries, Jr. et al. |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 2001/0009610 A1 | 7/2001 | Augustine |
| 2002/0041621 A1 | 4/2002 | Faries et al. |

| | | |
|---|---|---|
| 2002/0156451 A1 | 10/2002 | Lenker |
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0222933 A1 | 12/2003 | Choi |
| 2003/0231990 A1 | 12/2003 | Faries, Jr. et al. |
| 2004/0170409 A1 | 9/2004 | Faries, Jr. et al. |
| 2004/0189258 A1 | 9/2004 | Lehmann et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2006/0020255 A1 | 1/2006 | Cassidy et al. |
| 2006/0253075 A1 | 11/2006 | Faries, Jr. et al. |
| 2007/0000910 A1 | 1/2007 | Faries, Jr. et al. |
| 2007/0106243 A1 | 5/2007 | Faries, Jr. et al. |
| 2007/0161952 A1 | 7/2007 | Faries, Jr. et al. |
| 2007/0215018 A1 | 9/2007 | Faries, Jr. et al. |
| 2008/0147016 A1 | 6/2008 | Faries et al. |
| 2008/0205481 A1 | 8/2008 | Faries et al. |

FOREIGN PATENT DOCUMENTS

| | | |
|---|---|---|
| FR | 2711393 A1 | 4/1995 |
| FR | 2786057 | 5/2000 |
| GB | 2029677 A | 3/1980 |
| WO | WO 98/38953 | 9/1998 |
| WO | WO 99/22786 | 5/1999 |
| WO | WO 99/26690 | 6/1999 |
| WO | WO 99/58177 | 11/1999 |

OTHER PUBLICATIONS

Minco Products, Inc., *Bulletin CT198*, 1996.

Eurotherm Controls, Inc., *Model 2116 Temperature Controller*, 1997.

Ellenwood, *Drop Detector*, IBM Technical Bulletin, vol. 12, No. 5, Oct. 1969.

CBi Medical, Inc., *IV Fluid Warmer Model 8362*, 1992.

\* cited by examiner

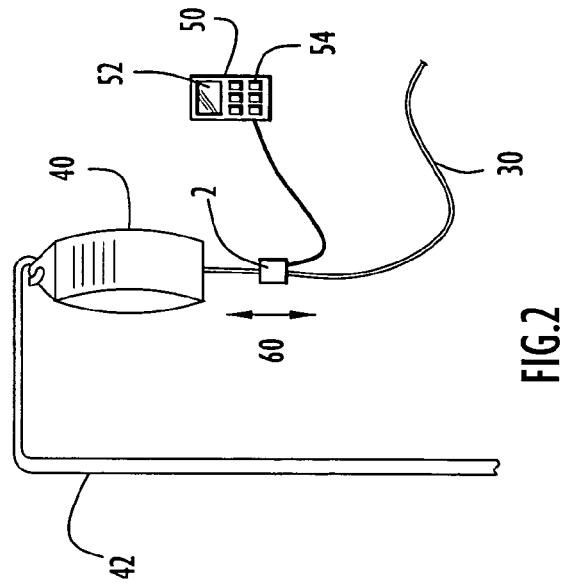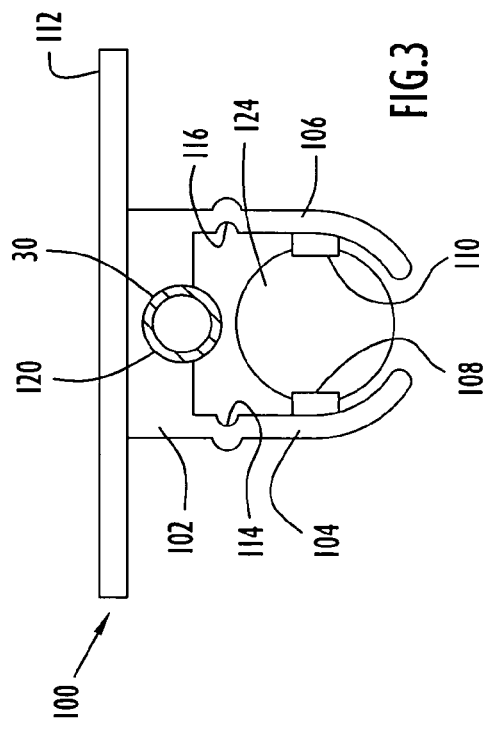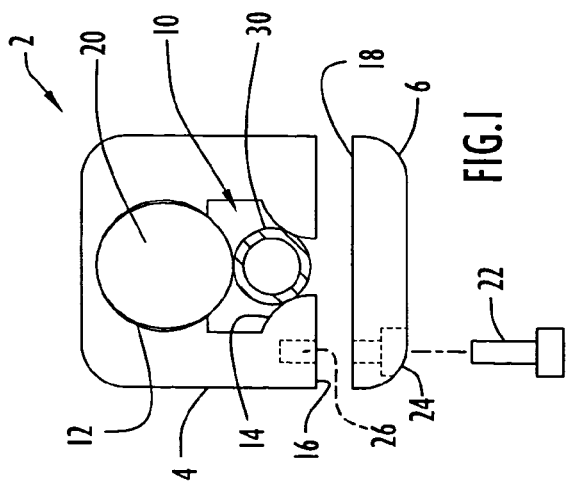

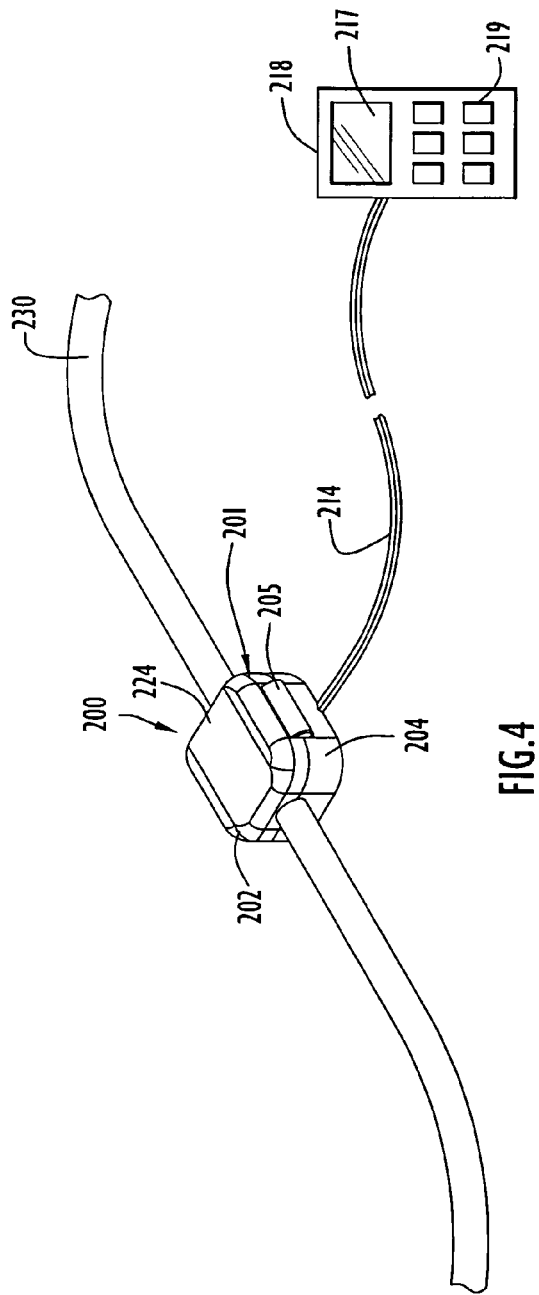
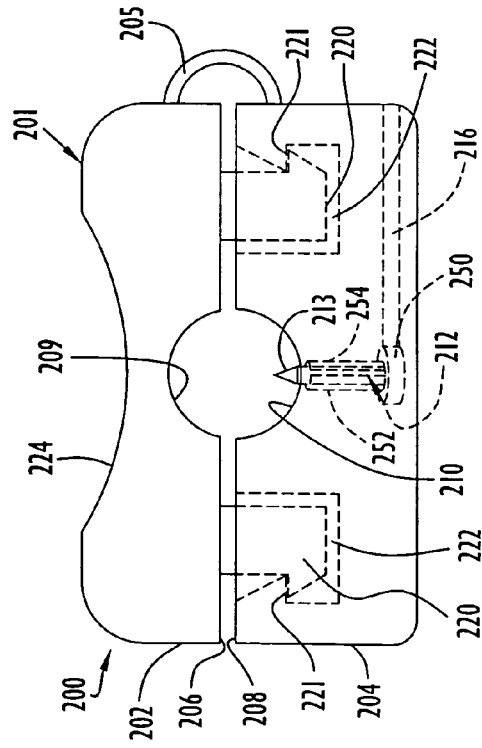
FIG. 4
FIG. 5

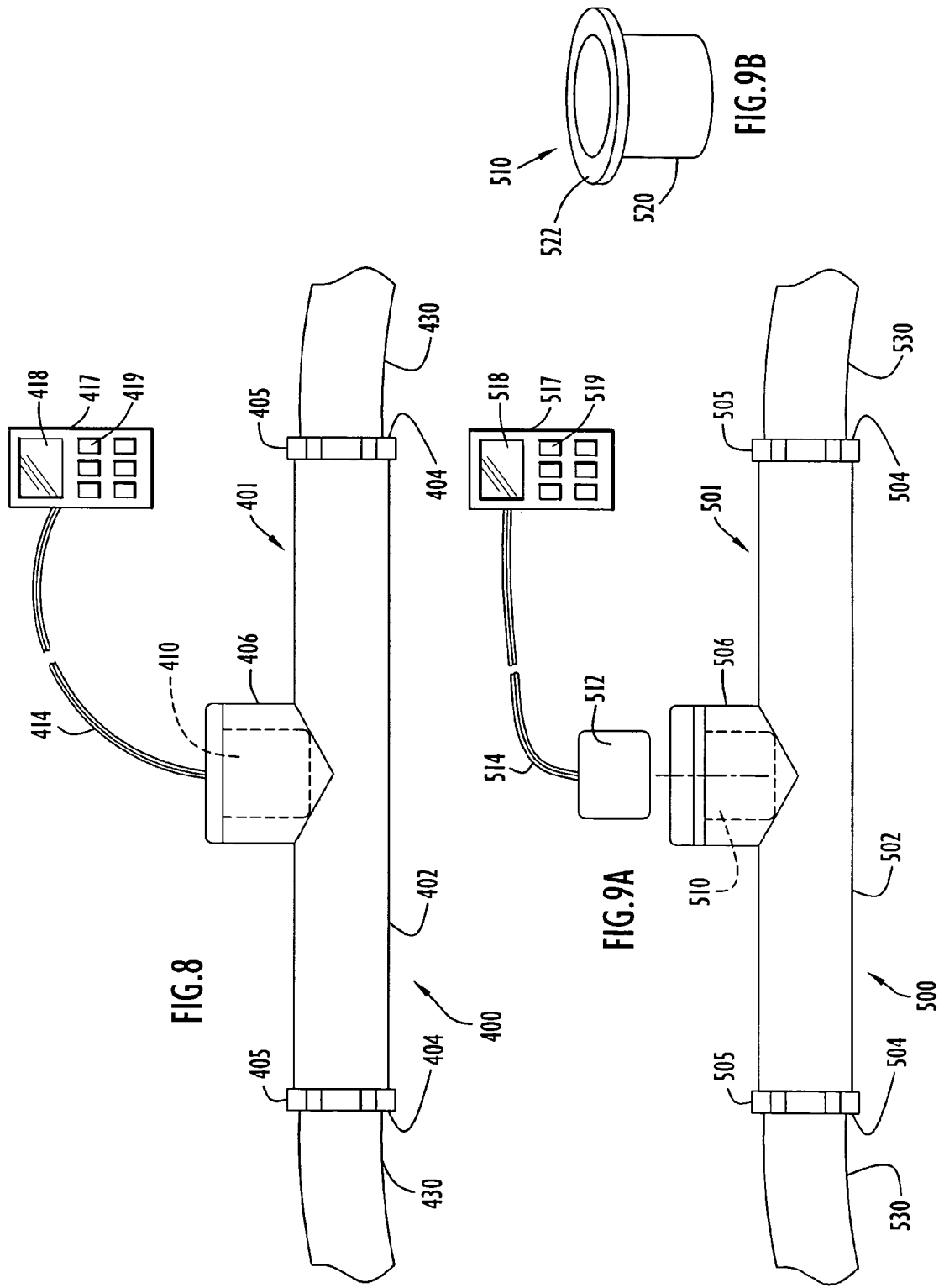

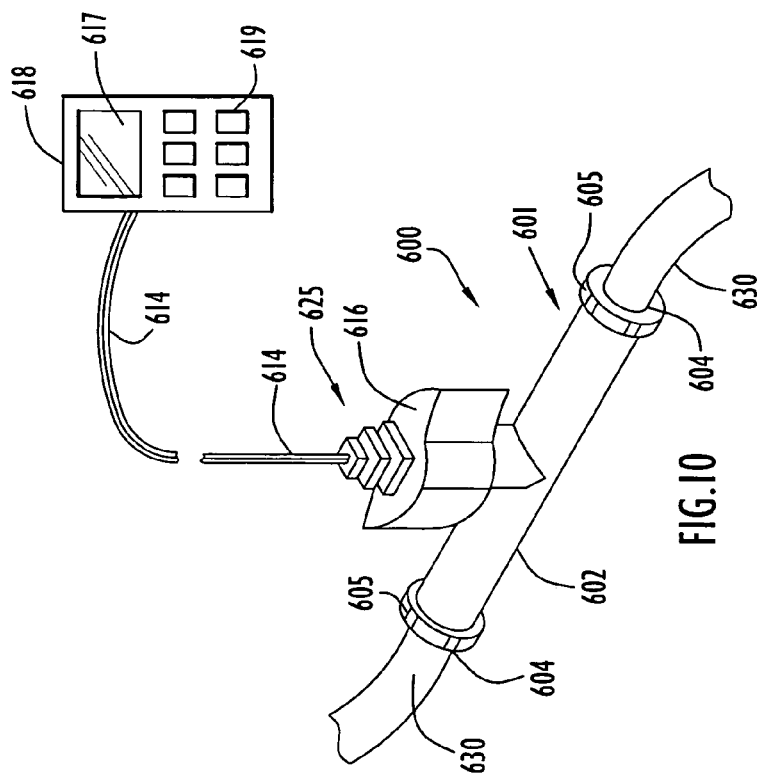
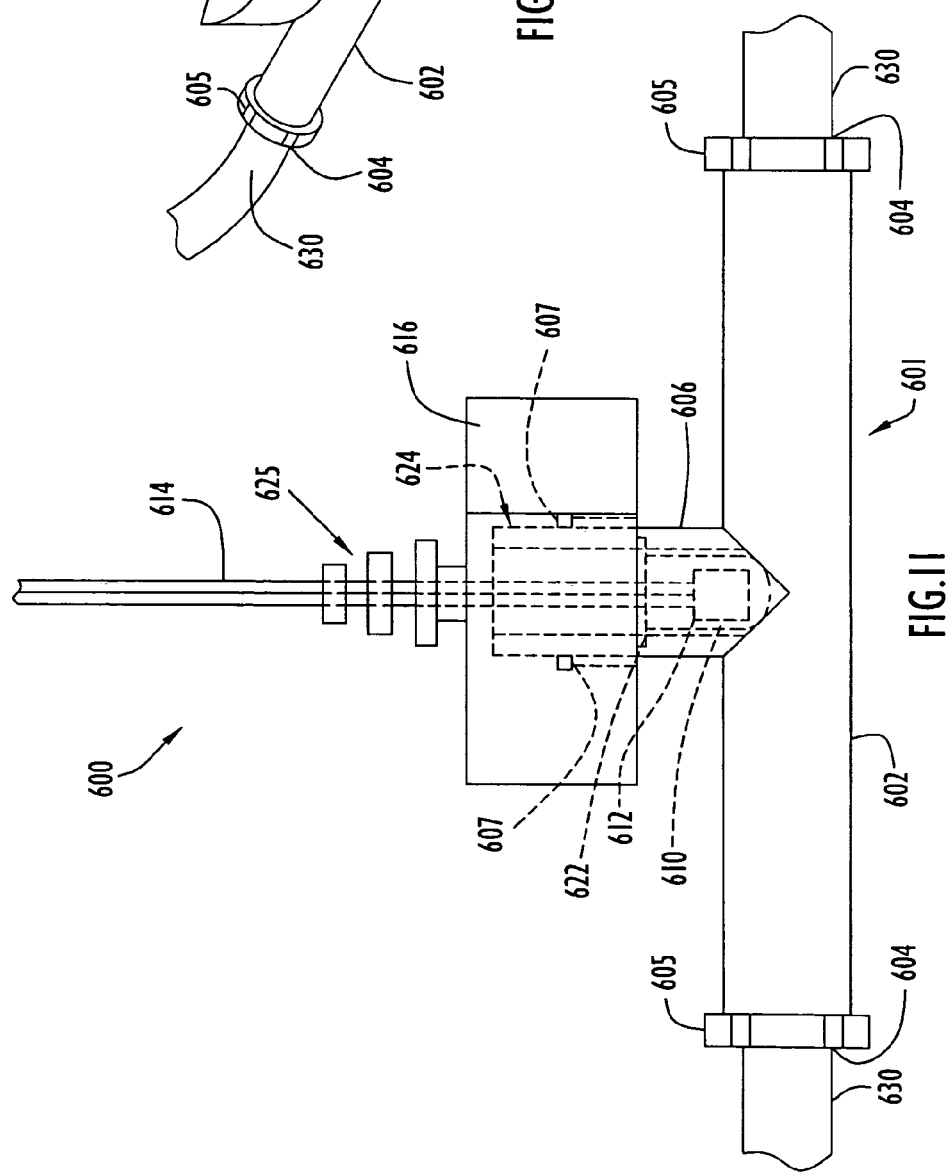
FIG.10
FIG.11

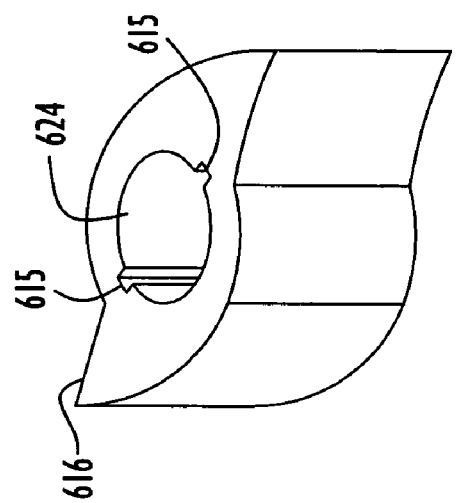
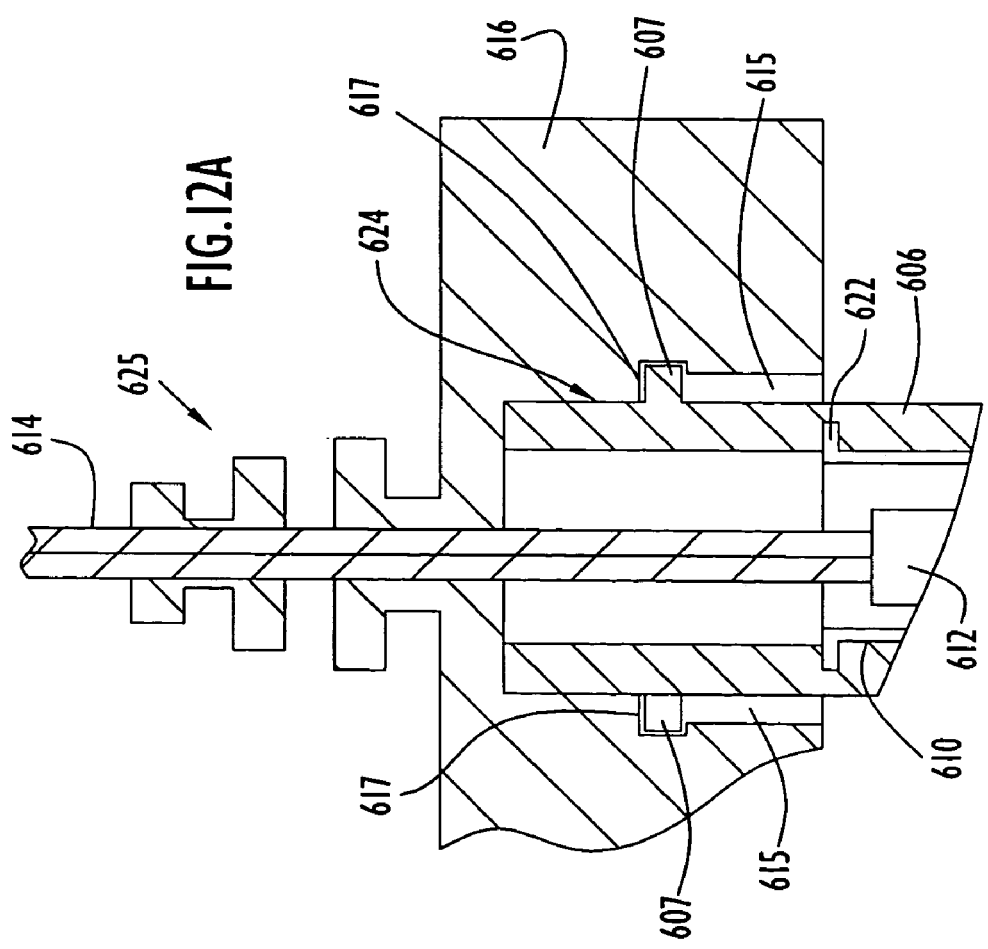

TEMPERATURE SENSING DEVICE FOR SELECTIVELY MEASURING TEMPERATURE AT DESIRED LOCATIONS ALONG AN INTRAVENOUS FLUID LINE

CROSS REFERENCE TO RELATED APPLICATIONS

This application is a divisional of U.S. patent application Ser. No. 09/973,988, entitled "Temperature Sensing Device for Selectively Measuring Temperature at Desired Locations Along an Intravenous Fluid Line" and filed Oct. 11, 2001, now U.S. Pat. No. 7,090,658, which is a continuation-in-part of U.S. patent application Ser. No. 09/380,507, filed Apr. 24, 2000, entitled "Method and Apparatus for Pressure Infusion and Temperature Control of Infused Liquids", now U.S. Pat. No. 6,824,528 which is a National Stage Application of PCT International Application No. PCT/US98/04199, filed Mar. 3, 1998, entitled "Method and Apparatus for Pressure Infusion and Temperature Control of Infused Liquids", which claims priority from U.S. Provisional Patent Application Ser. Nos. 60/040,885, filed Mar. 3, 1997, entitled "Method and Apparatus for Measurement and Control of Temperature for Infused Liquids" and 60/062,315, filed Oct. 17, 1997, entitled "Method and Apparatus for Pressure Infusion and Temperature Control of Infused Liquids". The disclosures of the foregoing patent applications are incorporated herein by reference in their entireties.

BACKGROUND OF THE INVENTION

1. Technical Field

The present invention pertains to temperature sensing devices for monitoring temperature of intravenous fluid. In particular, the present invention pertains to temperature sensing devices that monitor the temperature of intravenous fluids at any desirable location along a fluid line (e.g., an intravenous fluid line) to ensure a desired fluid temperature is maintained within the fluid line prior to entering a patient.

2. Discussion of Related Art

Intravenous (IV) fluids are typically infused within a patient utilizing a liquid filled bag or container and an IV fluid line for delivering fluids under gravity and/or applied pressure from the container to the patient. It is important in many situations that the temperature of the fluid within the IV line be maintained within a desirable and safe temperature range upon entering the patient so as to eliminate any potential for thermal shock and injury to the patient by the fluid.

Accordingly, the related art provides several devices that employ temperature sensors to monitor and/or control the temperature of fluid flowing within an intravenous or other type of fluid line. For example, U.S. Pat. No. 5,729,653 (Magliochetti et al.) discloses a device for heating a fluid to a body temperature prior to delivery of the fluid to a patient. In one embodiment, a fluid to be warmed prior to delivery to a patient can be passed through a flow through chamber disposed in the fluid delivery line. An electrically resistive heating element for heating the fluid can be molded into the chamber to heat the fluid from room or ambient storage temperatures to a body temperature of the patient. A probe of a temperature monitoring element can be used to monitor the temperature of the fluid exiting the chamber. In another embodiment, this information can be relayed back to a controller for controlling the power to the resistance element, and hence, the temperature of the fluid. In still another embodiment, an infrared temperature sensor can be used for monitoring the temperature of the fluid exiting the chamber by scanning through a window in the chamber outlet port or elsewhere in the fluid line. The device may further include an LED two-digit display of the exiting fluid temperature for visual temperature monitoring.

U.S. Pat. No. 5,250,032 (Carter, Jr. et al.) discloses a heater for warming blood, plasma and other solutions flowing through an IV tube prior to entry into a patient. The heater is releasably secured to a patient and includes a housing having an elongated channel extending from one end of the housing to its other end. The channel is formed with an elongated slot against which a heating element is mounted. The heating element is controlled by a control circuit and powered by batteries. The control circuit may energize the heating element continuously or cyclically in response to sensed temperatures.

U.S. Pat. No. 3,526,134 (Schaus) discloses a thermobulb mount for holding a temperature sensing element in a pipeline so as to prevent damage to the element which might otherwise be caused by fluid flow within the pipeline. The mount includes a body having threaded ends for connection in series with a pipeline, an installation boss with a hole through which the sensing element extends and a recess formed on the inside of the pipeline opposite the boss for supporting an outboard end of the sensing element.

U.S. Pat. No. 5,829,880 (Diedrich) discloses a device including a T-type pipe combination including a medium conduction pipe and a connection piece projecting away from the pipe. The pipe is connected to tubing that supplies medium to and leads medium away from the pipe. A plug unit is disposed within the connection piece and includes a stopper supporting contact pins and a temperature sensor connected to those pins. The temperature sensor indirectly measures the temperature of the medium flowing through the pipe. An electrical bush part is further secured to the connection piece via a bracket and is connected to the contact pins. The bush part housing includes contact bushes with electrical connecting lines that extend externally of the housing through openings defined therein.

U.S. Pat. No. 4,138,890 (Brown) discloses a temperature indicating probe including a liquid-in-glass thermometer encased within a housing. The housing includes a series of tapered, cylindrical shaped portions separated by a step or shoulder, which are respectively insertable into variously sized standard medical appliance line openings or fittings, for sensing and indicating the temperature of the working fluids being carried through the line.

The related art suffers from several disadvantages. In particular, the Magliochetti et al. and Carter, Jr. et al. systems employ temperature measurement in combination with temperature control, thereby increasing system complexity and costs to employ those systems for temperature measurement functions. Further, the size and/or mounting requirements for those systems tend to restrict system application to particular sections of an IV line. Thus, operators are required to estimate, or adjust system settings to compensate for, conditions at desired IV line sites outside the system application range. This tends to lead to inaccuracies in fluid temperature control and measurement for the desired sites, thereby risking injury to a patient. In addition, the Carter, Jr. et al. system measures temperature for temperature control of fluid without providing any temperature indication to an operator, thereby enabling infusion of fluid of unknown temperature into a patient.

The Schaus, Hollweck et al. and Diedrich devices are designed for non-medical fluid systems. Accordingly, these devices are employed for non-sterile applications and are ill-suited for medical applications that require sterility.

Although these devices measure fluid temperature, the devices generally do not provide a displayed temperature to an operator. Thus, fluids may attain inappropriate temperatures without notice to the operator which may lead to undesirable conditions or consequences. The Brown device requires an operator to manually observe a thermometer and determine a fluid temperature therefrom. This is distracting to the operator and permits possible operator error to be introduced with respect to the fluid temperature measurement, thereby enabling infusion of fluid at an inappropriate temperature and risking injury to the patient.

OBJECTS AND SUMMARY OF THE INVENTION

Accordingly, it is an object of the present invention to measure the temperature of a fluid within an IV line via a temperature sensing device selectively securable to a desired site along that line.

It is another object of the present invention to obtain an accurate and reliable temperature indication of fluid within an IV line at any desired location along that line and display the temperature indication to an operator.

Yet another object of the present invention is to removably secure a temperature sensing device to an IV line and facilitate measurement of fluid temperatures at varying locations along that line.

Still another object of the present invention is to facilitate re-use of a temperature sensor with a temperature sensing device to measure the temperature of sterile fluid while maintaining fluid sterility.

A further object of the present invention is to measure and display the temperature of fluid within an IV line via a line fitting employing a temperature sensor coupled to a display device.

The aforesaid objects may be achieved individually and/or in combination, and it is not intended that the present invention be construed as requiring two or more of the objects to be combined unless expressly required by the claims attached hereto.

According to the present invention, a temperature sensing device measures the temperature of a fluid at selected locations along an IV fluid line. The device is secured to a selected portion of the IV line and includes a temperature sensor for measuring fluid flowing within that line. The device is coupled to a temperature display device in communication with the temperature sensor to provide an indication of measured fluid temperature to an operator. The temperature sensing device may include a housing removably secured to a selected portion of the IV line. The housing includes a pivotable lower cover to engage the line and a temperature sensor disposed proximate the engaged line section to indirectly measure fluid temperature. The temperature sensor is coupled to a temperature display device to display the measured temperature to an operator.

Alternatively, the device may be in the form of a holder secured to a selected portion of the IV line. The holder is movable along the line and includes a temperature sensor disposed proximate the line to indirectly measure fluid temperatures at line locations secured to the holder. The temperature sensor is coupled to a temperature display device to display the measured temperature to an operator.

The temperature sensing device may alternatively include a housing with upper and lower members pivotally connected to each other and receiving an IV line therebetween. The lower member includes a temperature sensing tip configured to pierce the secured portion of the IV line. The tip directly contacts and measures temperature of fluid within the line, and is coupled to a temperature display device to display the measured temperature to an operator. Further, the temperature sensing device may include a resilient member having a spiral or overlapping configuration to surround a selected portion of the IV line. The resilient member includes a temperature sensing tip configured to pierce the selected IV line portion. The tip directly contacts and measures temperature of fluid within the line, and is coupled to a temperature display device to display the measured temperature to an operator.

The temperature sensing device may be in the form of a fitting securable to selected portions of the IV line. The fitting may be a 'T'-type fitting including a fluid conduit and a projection including a thermally conductive receptacle to receive a temperature sensor. The receptacle is disposed in direct contact with the fluid to enable temperature measurement by the temperature sensor. The sensor may alternatively be disposed in direct contact with the fluid (e.g., without employing the receptacle), while a securing mechanism may further be employed to releasably secure the temperature sensor to the fitting. The temperature sensor is coupled to a temperature display device to display the measured temperature to an operator. Alternatively, the fitting may be a 'Y'-type fitting and include a temperature sensor configured in the form of a syringe or needle for insertion into a fitting branch to measure fluid temperature. The sensor is coupled to a temperature display device to display the measured temperature to an operator. The sensor may further be employed with a sheath to permit re-use of the sensor while maintaining fluid sterility.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 1 is an exploded front view in elevation and partial section of a temperature sensing device attached to an IV fluid line in accordance with the present invention.

FIG. 2 is a view in perspective of the temperature sensing device of FIG. 1 coupled to a temperature display device for use with an infusion apparatus in accordance with the present invention.

FIG. 3 is a front view in elevation and partial section of a temperature sensing device for an IV fluid line in the form of a holder in accordance with the present invention.

FIG. 4 is a view in perspective of a temperature sensing device including a housing securable to an IV fluid line to measure temperature of fluid therein in accordance with the present invention.

FIG. 5 is a front view in elevation of a locking mechanism of the temperature sensing device of FIG. 4.

FIG. 8 is a view in perspective of a temperature sensing device for an IV fluid line in the form of a line fitting in accordance with the present invention.

FIG. 9A is an exploded view in perspective of a temperature sensing device in the form of a line fitting and including a thermally conductive receptacle for receiving a temperature sensor in accordance with the present invention.

FIG. 9B is a view in perspective of the thermally conductive receptacle of the temperature sensing device of FIG. 9A.

FIG. 10 is a view in perspective of a temperature sensing device including a securing mechanism in accordance with the present invention.

FIG. 11 is a side view in elevation of the temperature sensing device of FIG. 10.

FIG. 12A is a side view in elevation and section of the securing mechanism of the temperature sensing device of FIG. 10.

FIG. 12B is a bottom view in perspective of the securing mechanism of FIG. 12A.

DETAILED DESCRIPTION OF THE PREFERRED EMBODIMENTS

Figure 6:
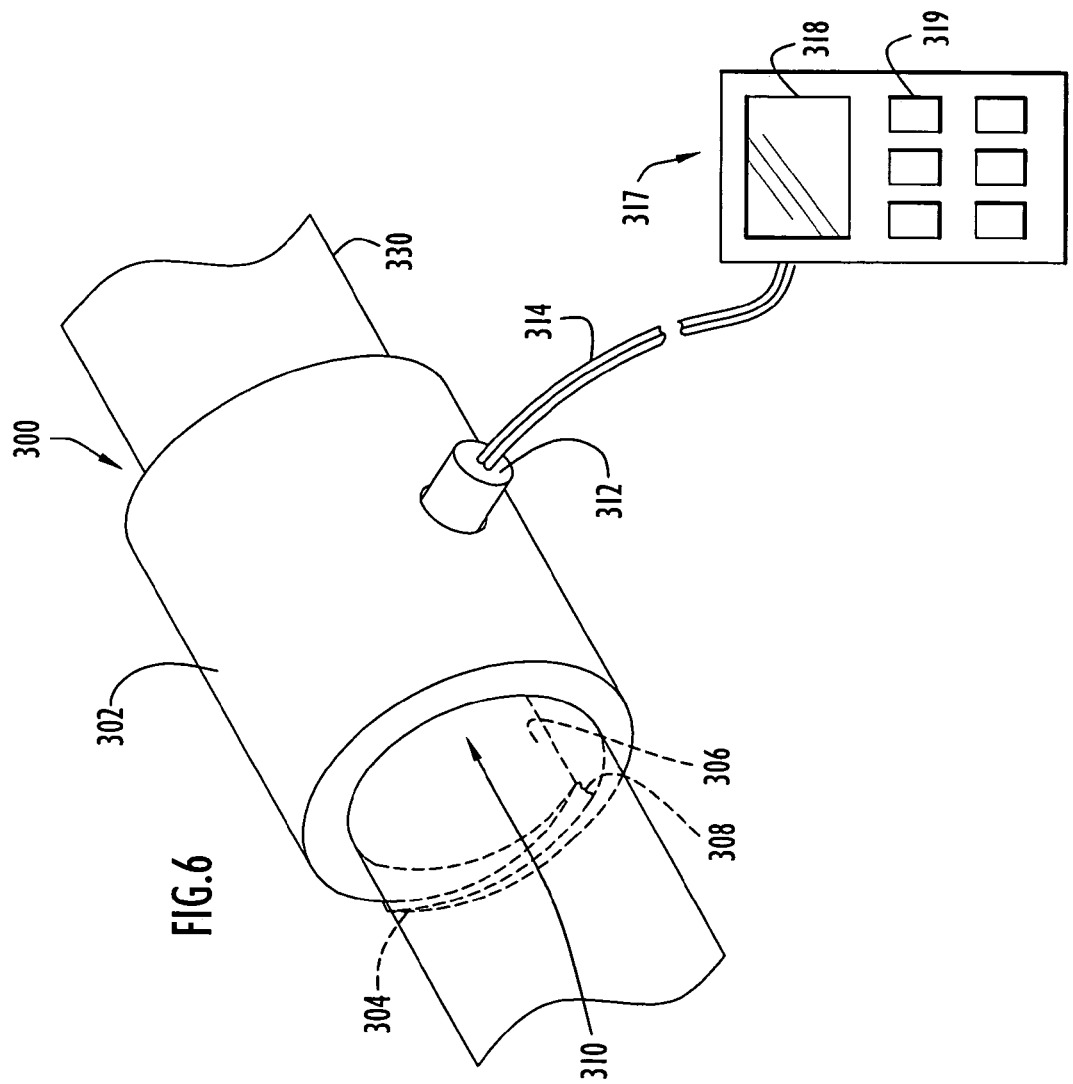
FIG. 6 is a view in perspective of a temperature sensing device for an IV fluid line including a spiral or overlapping configuration in accordance with the present invention.

A temperature sensing device for measuring the temperature of a fluid within an IV fluid line at operator selected locations along the line is illustrated in FIG. 1. Specifically, a temperature sensing device 2 may be removably affixed around any selected portion of an IV line 30. The device includes a housing member 4 and a cap member 6, wherein each member is typically constructed of an appropriate material (e.g., plastic) having suitable insulative properties to ensure the accuracy of temperatures measured for the portion of a fluid line disposed between the housing and cap members. Housing member 4 has a generally rectangular configuration and includes a channel 10 extending between the longitudinal ends of the housing member and having suitable dimensions to receive a selected portion of fluid line 30 and a temperature sensor 20. However, the housing member may have any geometric configuration suitable for operation of the device as described below. Channel 10 typically includes a sensor receiving area 12, a fluid line receiving area 14 and an open bottom portion defined in a bottom surface 16 of the housing member that provides access to the channel to permit an operator selected portion of IV line 30 to be received within fluid line receiving area 14. Sensor receiving area 12 has a configuration complimentary to temperature sensor 20 to receive and secure the temperature sensor therein. By way of example only, temperature sensor 20 and the sensor receiving area 12 include a generally cylindrical configuration. Fluid line receiving area 14 of channel 10 has a generally rectangular configuration and extends from a lower section of the sensor receiving area. The fluid line receiving area further includes a tapered section that narrows the channel toward bottom surface 16 of the housing member. The tapered section is further dimensioned to frictionally engage and secure the IV line within the device.

Temperature sensor 20 may be implemented by any type of conventional or other temperature sensor (e.g., RTD, IR, NTC, thermistors, thermocouples, etc.) suitable for operation of the device as described below. The temperature sensor may be secured within sensor receiving area 12 of the housing member channel in any suitable manner (e.g., adhesion, frictional engagement, etc.). The temperature sensor is positioned within the sensor receiving area and is disposed proximate and/or in direct contact with the IV line portion disposed within fluid line receiving area 14 to obtain a temperature measurement of fluid within that line.

Cap member 6 is generally rectangular and pivotally connected to the housing member bottom surface to secure a portion of the IV line within channel 10. The cap member basically facilitates insertion and removal of an IV line portion within the channel and may be connected to the housing member via a pin 22. The pin is inserted through a pivotal aperture 24 defined within the cap member toward a cap member front corner (e.g., front left corner as viewed in FIG. 1). Pin 22 extends through the cap member and is received within a pin receiving aperture 26 that is defined within housing member bottom surface 16 and substantially aligned with aperture 24. The pin may be secured within the pin receiving aperture in any suitable manner (e.g., threaded engagement, adhesion, etc.). The cap member pivotal aperture preferably includes transverse cross-sectional dimensions that are slightly greater than those of the pin to permit rotational movement of the cap member with respect to the pin and the housing member when the pin is secured within pin receiving aperture 26. Alternatively, the housing and cap members may be connected to each other via hinges or any other suitable connection mechanism.

The temperature sensing device is typically disposed along IV line 30 of an infusion apparatus as illustrated in FIG. 2. Specifically, the infusion apparatus includes an IV pole 42, a solution bag 40 suspended therefrom and IV line 30 enabling flow of solution from the solution bag to a patient. Sensing device 2 is disposed along line 30 and is in communication with a temperature display or monitor device 50 to provide an operator with indications of fluid temperature measurements at operator selected locations along the IV line. The monitor device may communicate with the fluid device in any suitable manner (e.g., electrical line, RF, IR, etc.). Monitor device 50 typically includes a temperature display 52 (e.g., LED or LCD), a plurality of input devices or buttons 54 and a processor to control monitor device operation and determine fluid temperature based on signals received from the temperature sensing device. The display typically indicates the temperature measured by temperature sensor 20, and may further indicate a desired or set-point temperature entered by the operator via buttons 54. The monitor device may further provide an indication when the temperature measured by sensor 20 falls within a desired range of the set-point temperature. In addition, the monitor device may include a printer and/or data recorder to print and/or record data associated with the measured IV fluid temperature. Exemplary monitor devices for use with the temperature sensing device include a Fluke 50S hand-held thermometer available from Fluke Corporation and a printing thermometer available from Extech Instruments.

Operation of the temperature sensing device is described with reference to FIGS. 1-2. Initially, an operator rotates cap member 6 with respect to housing member 4 to expose channel 10. If temperature sensor 20 is not already disposed within the housing member, the sensor may be inserted and secured within sensor receiving area 12. The temperature sensing device is subsequently secured to IV line 30 by inserting a selected portion of the IV line within fluid line receiving area 14 of housing member channel 10 such that part of the IV line wall frictionally engages the tapered section within the channel. Upon securing the IV line portion within the channel, cap member 6 is maneuvered to secure the IV line within the temperature sensing device. Temperature sensor 20 measures the temperature of fluid within the secured IV line portion and provides temperature measurements to monitor device 50 for display to an operator. The temperature sensing device may further provide temperature measurements of fluid at other locations within the IV line by placing the device at any location along the IV line (e.g., as shown by arrow 60 in FIG. 2) as described above. For example, temperature sensing device 2 may be placed along IV line 30 toward IV solution bag 40 on IV pole 42 or, alternatively, toward the infusion point on the subject (not shown). Thus, the device allows the operator to determine the fluid temperature at any point along the IV line with minimal disruption to the infusion procedure. The temperature sensing device further ensures proper mounting of the temperature sensor with respect to the IV line, thereby enabling a precise temperature measurement of fluid (i.e., not skin or ambient temperature) at specific locations within the IV line. The temperature sensing device may be removed from the IV line by moving cap member 6 with respect to housing member 4 to expose channel 10, and removing the secured portion of IV line 30 from the channel. The temperature sensing device may subsequently be removably attached to and utilized with additional IV lines without compromising sterility of the fluid.

A temperature sensing device in the form of a holder is illustrated in FIG. 3. Specifically, device 100 includes a substantially flat rectangular base 102 having curved prongs 104, 106 extending away from the base and curving toward each other. A generally rectangular platform 112 is attached to base 102 and has dimensions that are greater than those of the base. The platform may include various fastening mechanisms (e.g., hook and loop fasteners, tape, gel, etc.) and may be fastened to a patient (e.g., an arm or other body portion) during temperature measurement along the IV line. Prongs 104, 106 are resilient and may be spread from each other slightly to allow insertion of a portion of the IV line and the temperature sensor therebetween as described below. Prongs 104, 106 each respectively include a longitudinally extending groove 114, 116 and a transversely extending projection 108, 110. The grooves are defined in the prongs between projections 108, 110 and base 102, while the projections extend from the distal sections of the respective prongs toward each other. The projections basically serve as a stop to guide the temperature sensor in an appropriate position within device 100.

A groove or channel 120 is defined in base 102 and extends in a longitudinal direction. The groove is dimensioned to receive and engage a selected portion of IV line 30. A temperature sensor 124 is dimensioned to be frictionally retained between prongs 104, 106 with sensor portions disposed within grooves 114, 116 and projections 108, 110 serving as a stop for the temperature sensor. The temperature sensor is disposed proximate the IV line portion located within groove 120. Thus, the temperature sensor engages and is in direct contact with the IV line portion disposed within channel 120 to obtain an accurate temperature measurement of the liquid flowing within that IV line portion. The temperature sensor is substantially similar to and functions in substantially the same manner as the temperature sensor described above. In operation, temperature sensor 124 is typically inserted between prongs 104, 106 after insertion of a portion of fluid line 30 within groove 120 of base 102. Placement of the sensor between the prongs allows the device to slide along the IV line while maintaining direct contact between the sensor and the IV line. A temperature display or monitor device (not shown), substantially similar to the monitor device described above, is in communication (e.g., via a wire, RF or IR communication, etc.) with temperature sensor 124 to display temperature of fluid within the secured IV line portion measured by the temperature sensor.

The temperature sensing device may provide a direct measurement of fluid temperature within a selected portion of the IV line by puncturing the line with a temperature sensing probe as illustrated in FIGS. 4-5. Specifically, temperature sensing device 200 is securable to an operator selected portion of an IV line 230. The device includes a generally rectangular housing 201 with an upper member 202 and a lower member 204. The upper and lower members are generally rectangular with rounded corners and are pivotally connected to each other at corresponding sides via a hinge member 205. This allows selective engagement between an internal surface 206 of upper member 202 and an internal surface 208 of lower member 204 as described below. However, the upper and lower members may be connected to each other in any suitable manner to facilitate opening and closing of the housing. The lower and upper members of the housing may be constructed of any suitable rigid materials (e.g., plastic, metal, etc).

A generally semi-circular groove 209 is defined within the internal surface of the upper member, while the lower member internal surface includes a generally semi-circular groove 210 defined therein in substantial alignment with groove 209. The grooves extend along their respective internal surfaces between the longitudinal ends of the upper and lower members to collectively form a longitudinal channel through the housing when the upper and lower members engage each other. The longitudinal channel is appropriately dimensioned to receive a selected portion of IV line 230 for directly measuring temperatures of fluids flowing within the received IV line portion.

A temperature probe 212 is embedded within lower member 204 and extends from groove 210 toward an opposing, external surface of the lower member. Specifically, the probe includes a base 250, supports 252, 254 and a sensing tip 213. Base 250 is substantially cylindrical in the form of a disk and includes supports 252, 254 disposed on the base top surface. The supports are generally semi-circular and each have dimensions less than those of the base in order to reside on the base top surface. Sensing tip 213 is substantially cylindrical including a tapered distal end configured in the form of a spike and dimensions greater than those of the supports. The sensing tip is disposed on the base top surface between supports 252, 254. The supports encompass the sensing tip proximal portion while the tip distal portion extends from the distal ends of the supports through the lower member internal surface and within groove 210. Sensing tip 213 is preferably constructed of stainless steel and is configured to pierce the wall of the IV line when the line is inserted into the housing and the housing is subsequently manipulated to a closed state. Alternatively, sensing tip 213 may project slightly from groove 210 to obtain a temperature measurement by contacting (e.g., without piercing) the IV line. The temperature sensing tip may be implemented by any conventional or other type of temperature sensor (e.g., RTD, IR, NTC, thermistor, thermocouple, etc.) for direct measurement of fluid temperatures within the IV line. Sensor wiring 214 is connected to base 250 and extends within lower member 204. The sensor wiring emerges from a side portion of the lower member below hinge member 205 and is coupled to a temperature display or monitor device 217. The sensor wiring transmits signals indicating temperature information from the temperature probe to the monitor device. The monitor device is substantially similar to the monitor devices described above and includes a digital display 218 (e.g., LCD or LED) for displaying measured temperatures and input devices 219 in the form of buttons for controlling temperature values displayed on the digital display. The monitor device may further print, record or provide indications of temperature measurements as described above.

Locking tabs 220 extend from the upper member internal surface with groove 209 disposed between the tabs. Each locking tab 220 is aligned on internal surface 206 of the upper member with a corresponding generally L-shaped slot 222 defined in the lower member internal surface with groove 210 disposed between the slots. The locking tabs each include a shoulder portion 221 that engages with a lower base or "foot" portion of a corresponding L-shaped slot 222 to maintain the locking tabs within the slots in response to pressing the internal surfaces of the upper and lower members together. Alternatively, device 200 may include any other suitable locking mechanism to releasably or permanently lock the upper and lower members together. Upper member 202 further includes a depression 224 disposed and extending longitudinally on an upper member external surface. Depression 224 is suitably dimensioned to receive a digit of a user's hand (e.g., a thumb or forefinger) and provide an enhanced gripping surface for facilitating closure of the housing by pressing the upper and lower members together upon placement of a portion of an IV line therebetween. The housing may be disposable and configured for a single use, while the temperature probe may be removably disposed within the housing for re-use. In this case, the sensing tip may employ a thermally conductive and disposable cover for each use to maintain fluid sterility.

In operation, upper and lower members 202, 204 are separated from each other such that groove 210 on internal surface 208 of the lower member is exposed. A selected portion of IV line 230 is inserted into groove 210 so as to cover sensing tip 213, and upper member 202 is subsequently pivoted with respect to lower member 204 to align tabs 220 with slots 222. The upper member is pressed against the lower member (e.g., by using depression 224 as a gripping surface for the operator's thumb or forefinger) such that tabs 220 are pressed into slots 222 until shoulders 221 are locked therein. The pressing force of upper member 202 in a direction toward lower member 204 simultaneously forces the portion of IV line 230 disposed between the members toward the lower member internal surface by action of groove 209. This further causes sensing tip 213 to pierce the IV line for direct exposure to IV fluid therein. The sensing tip provides a fluid tight seal between the temperature sensing device and the IV line once the line is pierced. Sensor wiring 214 is subsequently connected to temperature display or monitor device 217 to facilitate display of IV line fluid temperature measured by temperature probe 212.

Figure 7:
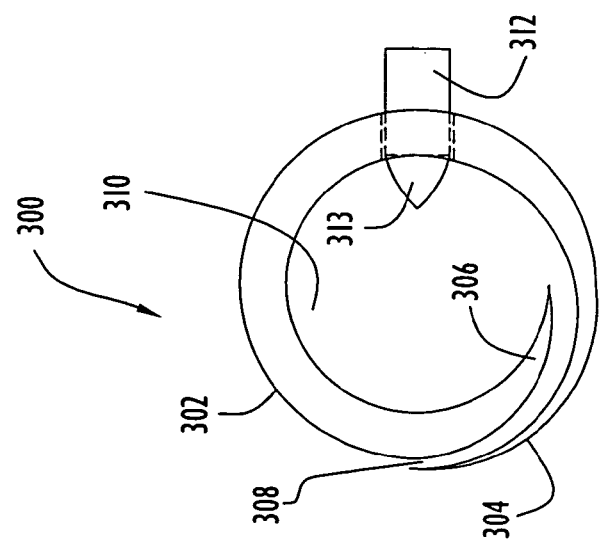
FIG. 7 is a front view in elevation of the temperature sensing device of FIG. 6.

A temperature sensing device of the present invention including a spiral or overlapping configuration is illustrated in FIGS. 6-7. Specifically, a temperature sensing device 300 includes a generally cylindrical resilient member 302 including a longitudinal channel 310 defined therethrough. The channel includes dimensions sufficient to receive an operator selected portion of an IV line 330. The resilient member is noncontinuous along its exterior surface and includes an exterior end portion 304 and an opposing interior end portion 306. The exterior and interior end portions overlap, while the resilient member thickness tapers toward the overlapping end portions, thereby forming a narrow gap 308 therebetween. Resilient member 302 is constructed of a resilient material (e.g., plastic) that enables end portions 304, 306 to be separated from each other and facilitate insertion of the IV line within channel 310. A temperature probe 312 is disposed through resilient member 302 and into channel 310. The probe terminates in a sensing tip 313 configured as a spike to pierce the wall of the IV line inserted within the channel. The resilient member has sufficient resiliency to drive the sensing tip through and pierce the line. Alternatively, the resilient member may include a force application mechanism to provide sufficient force to enable sensing the tip to pierce the line. The sensing tip may alternatively obtain a temperature measurement by contacting (e.g., without piercing) the IV line. The temperature probe further includes sensor wiring 314 extending to a temperature display or monitor device 317 for displaying temperatures measured by the probe in substantially the same manner described above. The temperature probe may be implemented by any conventional or other temperature sensors (e.g., RTD, IR, NTC, thermistor, thermocouple, etc.). The monitor device is substantially similar to the monitor devices described above and includes a digital display 318 for displaying measured temperatures and input devices 319 in the form of buttons for controlling temperature values displayed on the digital display. The monitor device may further print, record and/or provide various temperature indications as described above.

In operation, end portions 304, 306 are separated to enable insertion of an operator selected portion of IV line 330 within channel 310. The selected IV line portion is inserted between the separated end portions and into gap 308 while device 300 is manipulated (e.g., by rotating resilient member 302 around the IV line) to force the IV line into channel 310. As the IV line enters the channel, sensing tip 313 engages and pierces an exterior surface of the IV line to directly contact fluid therein. Thus, the device functions to retain the sensing tip against the IV line to facilitate temperature measurements of fluid flowing within the IV line. Temperature measurement information is transmitted to monitor device 317 to provide various temperature indications to an operator as described above.

A temperature sensing device of the present invention in the form of a fitting securable to an IV line to measure fluid temperature is illustrated in FIG. 8. Specifically, a temperature sensing device 400 includes a fitting 401 including a substantially cylindrical base portion 402 and a generally cylindrical projection 406 extending transversely from an intermediate section of the base portion. The base portion includes open ends 404 and a longitudinal channel defined therethrough to permit fluid flow through the base portion. The open ends are securable to selected portions of an IV line 430. The projection similarly includes open ends and facilitates access to the base portion channel. The fitting typically includes a T-type configuration, however, any configuration (e.g., a Y-type fitting, cross fitting, coupling, etc.) may be utilized. Each base portion open end 404 is typically releasably secured to the IV line via a Luer lock 405 or any suitable connector, while the fitting is typically disposable after each use to maintain fluid sterility. Alternatively, the fitting may be permanently secured to the IV line (e.g., by welding the ends of the fitting to portions of the IV line) to form a disposable IV line set. The fitting may be constructed of plastic or any other rigid material suitable for use with IV lines.

Projection 406 serves to engage and secure a temperature sensor within the fitting. Specifically, a temperature probe 410 is disposed within projection 406 and extends partially within base portion 402. Temperature probe 410 may be implemented by any conventional or other temperature sensor (e.g., RTD, IR, NTC, thermistor, thermocouple, etc.) and may be secured within the projection via any securing mechanisms (e.g., friction fit, adhesives, etc.). The probe is disposed within the projection in a manner that provides a fluid tight seal with the fitting channel to maintain IV fluid within the fitting. Sensor wiring 414 is connected to probe 410 and extends from the fitting to a temperature display or monitor device 417. The monitor device is substantially similar to the monitor devices described above and includes a digital display 418 for displaying measured temperatures and input devices 419 in the form of buttons for controlling temperature values displayed on the digital display. The monitor device may further print, record and/or provide various temperature indications as described above.

In operation, device 400 is attached to an IV line by securing base portion open ends 404 to operator selected portions of IV line 430. Upon securing the fitting to the IV line in a fluid tight relationship, IV fluid is permitted to flow through the IV line and fitting. Sensor wiring 414 is connected to temperature monitor 417. Temperature probe 410 contacts fluid flowing through the fitting and directly measures the temperature of the fluid. The probe transmits the measured temperature information via the sensor wiring to the monitor device for display of fluid temperature. Upon completion of an IV fluid temperature measurement or medical procedure, the sensor wiring may be disengaged from the monitor, while the fitting is removed from the IV line and discarded.

The temperature sensing fitting may alternatively facilitate releasable engagement of the temperature probe as illustrated in FIGS. 9A-9B. Specifically, a sensing device 500 includes a fitting 501 with substantially the same configuration as fitting 401 described above. Fitting 501 includes a substantially cylindrical base portion 502 and a generally cylindrical projection 506 extending transversely from an intermediate section of the base portion. The base portion includes open ends 504 and a longitudinal channel defined therethrough to permit fluid flow through the base portion. The projection includes open ends and facilitates access to the base portion channel. Base portion open ends 504 are securable to selected portions of an IV line 530 via Luer locks 505 or other connectors in substantially the same manner described above for device 400. A thermally conductive receptacle 510 is secured within projection 506 and extends partially within base portion 502 for contacting fluid flowing within the base portion channel. Receptacle 510 may be constructed of stainless steel or any other material having suitable thermal conductivity, and may be secured within the projection via any suitable securing techniques (e.g., friction fit, adhesives, etc.). The receptacle includes a generally cylindrical body 520 with a closed distal end that extends partially within the base portion and an open proximal end for receiving a temperature probe 512 as described below. A flange 522 extends radially from the open proximal end of the receptacle to engage an interior surface of the projection. The receptacle includes dimensions sufficient to provide a fluid tight seal between the projection and base portion channel to maintain fluid within the channel. A temperature probe 512 is removably inserted within the receptacle with the distal end of the probe in contact with the receptacle closed end. The probe may be secured within the receptacle via friction fit, a locking or securing mechanism or any other securing techniques. Sensor wiring 514 connects the probe to a temperature display or monitor device 517. The monitor device is substantially similar to the monitor devices described above and displays temperatures measured by temperature probe 512 on a digital display 518 in accordance with manipulation of input devices or buttons 519. The monitor device may further print, record and/or provide various temperature indications as described above. The probe may be re-used with new fittings, while the receptacle of each new fitting maintains the sterile field for fluid flowing within that fitting.

In operation, device 500 is attached to an IV line by securing base portion open ends 504 to selected portions of IV line 530. Upon securing the fitting to the IV line in a fluid tight relationship, IV fluid is permitted to flow through the line and fitting. As fluid flows within the fitting, the receptacle closed end contacts the fluid, while the receptacle conducts thermal energy. Temperature probe 512 is inserted into and contacts the closed end of receptacle 510 to measure the temperature of the receptacle. Temperature signals are transmitted from the probe through sensor wiring 514 to the monitor device for display of fluid temperature to the operator. After completion of an IV fluid temperature measuring or medical procedure, probe 512 is removed from receptacle 510 of the fitting, while the fitting may be discarded. Since the temperature probe does not directly contact fluid flowing within the IV line, the system facilitates repeated use of the probe with additional IV lines without the need for sterilization.

The temperature sensing device may employ a securing mechanism for releasably engaging a temperature probe as illustrated in FIGS. 10-11 and 12A-12B. Specifically, a sensing device 600 includes a fitting 601 with substantially the same configuration as fitting 501 described above. Fitting 601 includes a substantially cylindrical base portion 602 and a generally cylindrical projection 606 extending transversely from an intermediate section of the base portion. The base portion includes open ends 604 and a longitudinal channel defined therethrough to permit fluid flow through the base portion. The projection includes open ends and facilitates access to the channel. Base portion open ends 604 are securable to portions of an IV line 630 via Luer locks 605 or other connectors in substantially the same manner described above for device 500. A thermally conductive receptacle 610, substantially similar in configuration to receptacle 510 described above, is secured within projection 606 and extends partially within base portion 602 for contacting fluid flowing within the base portion channel. The receptacle includes a generally cylindrical body with a closed distal end that extends partially within the base portion and an open proximal end for receiving a temperature probe 612 as described below. A flange 622 extends radially from the open proximal end of the receptacle to engage an interior surface of the projection. The receptacle includes dimensions sufficient to provide a fluid tight seal between the projection and base portion channel to maintain fluid within the channel in substantially the same manner described above.

A temperature probe 612 is secured to fitting 601 and disposed within receptacle 610 via a securing member or cap 616. Specifically, cap 616 may be constructed of any suitable materials (e.g., plastic) and includes a generally S-shaped configuration with ends tapering in thickness to facilitate enhanced gripping. The cap includes a channel 624 defined in the cap interior and extending from a cap proximal portion to a cap distal surface. The channel is dimensioned to receive and retain the fitting projection. Temperature probe 612 is disposed within the cap channel and extends beyond the cap distal surface. The channel is dimensioned to receive and retain the fitting projection, while the probe includes transverse cross-sectional dimensions slightly less than those of receptacle 610 to enable insertion of the probe within the receptacle as described below. The cap proximal surface includes a support structure 625 disposed thereon to guide sensor wiring 614 and provide structural support for cap 616. Sensor wiring 614 is connected to probe 612 and extends from the probe through the cap proximal surface and support structure 625 to a temperature display or monitor device 617. The monitor device is substantially similar to the monitor devices described above and displays temperatures measured by temperature probe 612 on a digital display 618 in accordance with manipulation of input devices or buttons 619. The monitor device may further print, record and/or provide various temperature indications as described above.

Projection 606 further includes tabs 607 disposed toward the projection proximal end and angularly spaced apart by approximately one-hundred eighty degrees. Channel 624 includes transverse cross-sectional dimensions slightly greater than those of the projection, but less than those of the projection portions containing tabs 607. In order to accommodate the projection tab portions, channel 624 includes grooves 615 defined therein and angularly spaced apart by approximately one hundred eighty degrees. The grooves extend from the cap distal surface toward the channel proximal end and include dimensions suitable to accommodate the tabs. Recesses or notches 617 are defined at the proximal ends of the respective grooves and are dimensioned to receive and retain corresponding tabs 607. The transverse cross-sectional dimensions of the projection tab portions are slightly greater than those of the channel with grooves 615, but less than the dimensions of the channel with recesses 617. The grooves basically compress the projection tab portions due to projection resiliency to receive those portions in a snug fashion and to guide the tab portions toward recesses 617. The projection resiliency causes the projection to expand upon reaching recesses 617, thereby forcing tabs 607 in a locking engagement with those recesses. Locking of tabs 607 in corresponding recesses 617 assures that the temperature probe is positioned in contact with the receptacle within the projection. In addition, grooves 615 may taper in depth toward corresponding recesses 617 to assist in guiding tabs 607 through the grooves and into the recesses.

Tabs 607 are each configured to be fractured and removed from the fitting. This prevents the fitting from being re-used for temperature measurement, thereby maintaining fluid sterility. The tabs may be removed from the fitting by rotating the cap with respect to the projection when the tabs are disposed within recesses 617. The recesses inhibit tab motion, thereby enabling the rotational force applied to the cap to fracture and remove the tabs from the fitting. Recesses 617 may further be elongated transversely on the cap interior surface to permit initial free rotational movement of cap 616 and enhance application of rotational force to the cap for fracturing the tabs.

In operation, temperature device 600 is connected to an operator selected portion of IV line 630 as described above. Securing cap 616 is disposed over fitting projection 606 with temperature probe 612 disposed within the projection and channels 615 aligned with tabs 607. The cap is forced distally onto the projection to allow tabs 607 to travel proximally through channels 615 and be secured within recesses 617, while the temperature probe is inserted into receptacle 610. Upon securing the tabs within the recesses, the cap is effectively locked on the fitting with the temperature probe contacting the interior surface of receptacle 610. Fluid is permitted to flow within the fitting and directly contacts a surface of the receptacle closed end extending within base portion 602. The receptacle conducts thermal energy and the receptacle temperature is measured by the temperature probe and subsequently displayed on the monitor device. Once the temperature measurement or medical procedure is completed, the locking engagement between the cap and fitting may be released by rotating the cap relative to the projection. This causes the tabs to fracture and be removed from the projection, thereby disengaging the cap and temperature probe from the fitting. Thus, device 600 facilitates temperature measurement without direct contact of fluid and employs a temporary locking arrangement between the temperature probe and the fitting, thereby allowing reuse of the probe and securing cap with additional fittings without the need for sterilization. Further, the fitting is limited to a single use for temperature measurement to prevent contamination of sterile fluid. In addition, the tabs may notify an operator of fitting use. Basically, since the securing cap removes the projection tabs after use, the absence of those tabs on the fitting indicates that the fitting has been previously used and may compromise sterile conditions when used for another application.

Figure 13:
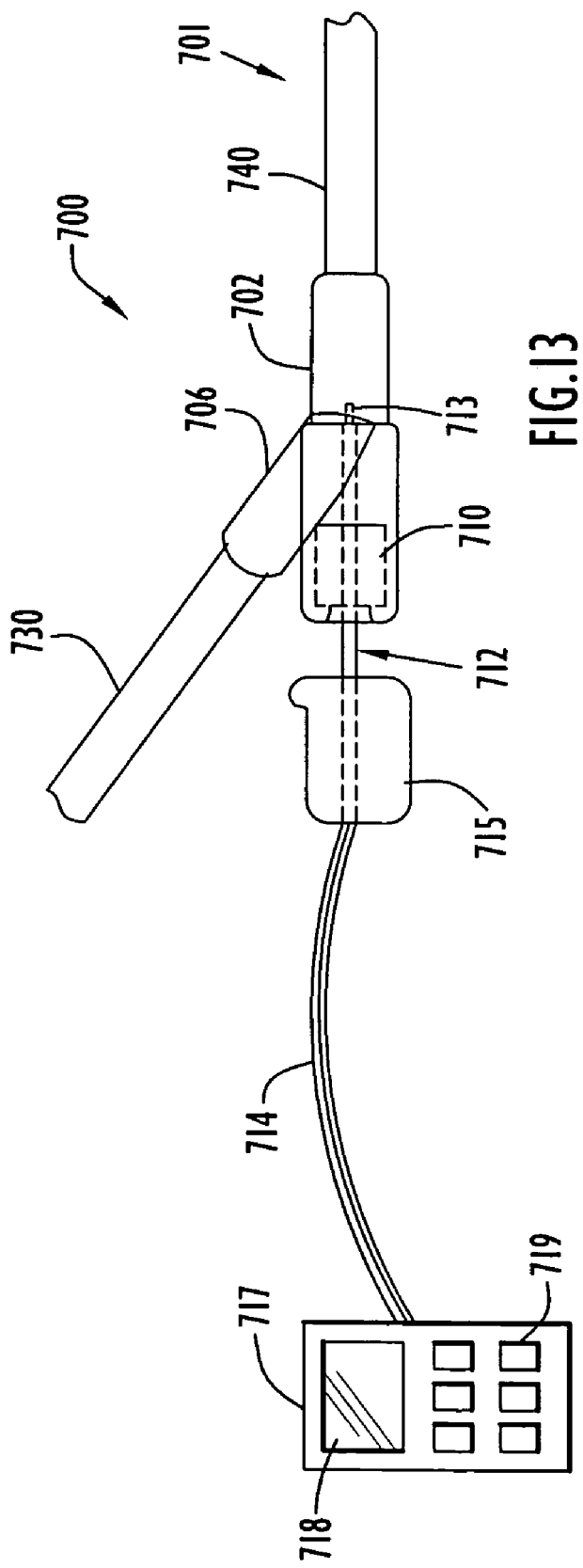
FIG. 13 is a view in perspective of a temperature sensing device including an alternative line fitting configuration in accordance with the present invention.

A temperature sensing device in the form of a fitting typically utilized for permitting injection of fluids into an IV line is illustrated in FIG. 13. Specifically, a temperature sensing device 700 includes a fitting 701 with a substantially cylindrical base portion 702 and a generally cylindrical inlet portion 706 extending from, and at an approximate forty-five degree angle relative to, an intermediate section of the base portion. The base and inlet portions each include a longitudinal channel defined therethrough to permit fluid flow through those portions. The fitting inlet portion receives an IV line 730 connected to a fluid source, while the base portion distal end is secured to an IV line 740 for conveyance of fluid to a patient. The fitting may be secured to the IV line portions via locks or connectors in substantially the same manner described above. The fitting typically includes a Y-type configuration, however, any type of fitting configuration may be employed.

The proximal section of the base portion includes transverse cross-sectional dimensions greater than those of the base portion distal section and houses a flexible membrane 710. The flexible membrane is constructed of a penetrable nylon or other suitable material that provides a barrier for permitting insertion and removal of a syringe needle or other instrument therethrough, while maintaining a fluid tight seal at the base portion proximal end. A temperature probe 712 is inserted through the membrane and into the fitting to measure the temperature of fluids flowing therein. In particular, probe 712 is configured in the from of a syringe needle and includes a sensing tip 713 disposed at a probe distal end and a handle 715 disposed at a probe proximal end. The handle provides a gripping surface for an operator when inserting the sensing tip through the membrane. The temperature probe may be implemented by any conventional or other temperature sensor (e.g., RTD, IR, NTC, thermistor, thermocouple, etc.). Sensor wiring 714 extends from the probe to a temperature display or monitor device 717. The monitor device is substantially similar to the monitor devices described above and displays the measured temperatures on a digital display 718 in accordance with manipulation of input devices or buttons 719. The monitor device may further print, record and/or provide various temperature indications as described above.

In operation, fitting 701 is secured to an operator selected portion of an IV line as described above. Temperature probe 712 is inserted through flexible membrane 710 at the base portion proximal end until sensing tip 713 is completely disposed within the fitting and in contact with fluid flowing therein. The probe is connected to the monitor device and fluid temperatures are measured and subsequently displayed as described above. Upon completion of a temperature measurement or medical procedure, the probe may be removed from the fitting and sterilized and reused. Alternatively, device 700 may include a sheath (not shown) constructed of stainless steel or any other suitable thermally conductive material to cover the sensing tip during use. The sheath maintains sterility of the fluid and permits reuse of the sensing tip without sterilization. The sheath may either be discarded or sterilized and reused after completion of a temperature measurement or medical procedure.

It will be appreciated that the embodiments described above and illustrated in the drawings represent only a few of the many ways of implementing a temperature sensing device for selectively measuring temperature at desired locations along an intravenous fluid line.

The temperature sensing device including the housing and cap members may be of any shape or size and may be constructed of any suitable materials. The device may be secured at any locations along an IV or any other fluid line. The housing and cap members may be of any quantity, shape or size, and may be constructed of any suitable materials. The housing member channel may be of any quantity, shape or size and may be defined within the housing member at any location and extend in any direction. The sensor and fluid line receiving areas may be of any quantity, shape or size, may be defined at any suitable locations and may receive the sensor and fluid line in any manner (e.g., friction fit, securing mechanism, etc.). The cap member may be attached to the housing member via any quantity of any type of fasteners or connectors or in any other manner. The pin and apertures may be of any quantity, shape or size. The apertures may be defined in the housing and cap members at any desired locations. The housing member may further include any suitable locking mechanism to releasably or non-releasably lock the fluid line within the housing member.

The temperature sensors or probes of the temperature sensing devices described above may be implemented by any quantity of any type of conventional or other temperature measuring devices (e.g., RTD, IR, NTC, thermistors, thermocouples, etc.). The sensors may be of any shape or size to accommodate a particular application. The temperature display or monitor devices described above may be implemented by any quantity of conventional or other processing devices or circuitry to determine and display fluid temperature. The display devices may include processors and various indicators (e.g., visual, audio, speech synthesis, etc.) to indicate the measured temperature and notify of occurrence of any type of temperature or other conditions. The temperature sensors may communicate with the display devices via any communications medium (e.g., wired, wireless, IR, etc.). The display devices may include any quantity of any type of conventional or other displays (e.g., LCD, LED, etc.) of any size or shape disposed at any suitable locations. The display devices may display any desired information (e.g., time, temperature, date, patient information, etc.), and may be disposed at any locations (e.g., near or away from the temperature sensing device) within view of an operator. The display device may employ any type of input devices (e.g., keypad, buttons, voice recognition, touch screen, etc.) and may further include any types of processing, printing and/or recording devices to process, print and/or record any desired information in any desired fashion.

The temperature sensing device in the form of a holder may be of any shape or size and may be constructed of any suitable materials. The base, platform and prongs may be of any quantity, shape or size, may be connected or arranged in any fashion and may be constructed of any suitable materials. The platform may include any quantity of any type of fastening mechanism (e.g., gel, adhesives, hook and loop fasteners, etc.) to secure the holder to any portion of a patient (e.g., arm, leg, etc.). The fastening mechanism may be disposed at any locations on the platform or holder. The grooves defined in the prongs may be of any quantity, shape or size, may be defined at any suitable locations and may extend in any desired direction. The prongs may include any suitable configuration and extend in any desired directions. The prong projections may be of any quantity, shape or size and may be disposed at any suitable locations on the prongs or holder. The base groove may be of any quantity shape or size, may be defined in the base or holder at any desired locations and may extend in any directions. The groove may receive and secure any type of fluid line in any desired manner (e.g., friction fit, securing mechanism, etc.). The holder may include any configuration to secure the temperature sensor and/or fluid line in any desired manner.

The temperature sensing device including the upper and lower members may be of any quantity, shape or size and may be constructed of any suitable materials. The upper and lower members may be of any quantity, shape or size and may be constructed of any suitable materials. The upper and lower members may be attached to each other via any type of conventional or other securing mechanism (e.g., hinges, brackets, etc.). The grooves defined in the upper and lower members may be of any quantity, shape or size and may be defined in the members at any desired locations and may extend in any desired directions. The grooves may form a channel of any quantity, shape or size to accommodate any type of fluid line. The temperature sensor may be of any quantity and may be disposed within the upper and/or lower member at any suitable locations. The temperature sensor base and supports may be of any quantity, shape or size and may be constructed of any suitable materials. The sensing tip may be of any shape or size, may be constructed of any suitably thermally conducting materials and may be configured and/or disposed to puncture and/or contact the fluid line to measure fluid temperature.

The tabs and slots of the upper and lower members may be of any quantity, shape or size and may be disposed on the upper and lower members at any desired locations. The upper and lower members may include any conventional or other locking mechanism to permanently or releasably secure the members together. The depression may be of any quantity, shape or size, may be disposed at any desired locations on the upper and/or lower members and may receive any quantity of portions of an operator body (e.g., hand, fingers, etc.). A cover may be employed for use with the temperature sensor to maintain fluid sterility and permit re-use of the sensor. The cover may be of any quantity, shape or size and may be constructed of any suitable thermally conducting materials.

The temperature sensing device including a spiral configuration may be of any quantity, shape or size and may be constructed of any suitable materials. The device may include any resilient member configured in any fashion to wrap around a fluid line. The channel may be of any shape or size and may extend in any desired direction. The gap between the member ends may include any suitable dimensions. The temperature probe may be disposed on or through the resilient member at any desired locations, while the sensing tip may be of any shape or size, may be constructed of any suitably thermally conducting materials and may be configured and/or disposed to puncture and/or contact the fluid line to measure fluid temperature. The sensing device may include any type of conventional or other force application mechanism (e.g., spring, driving mechanism, etc.) to drive the sensing tip to pierce the fluid line.

The temperature sensing device in the form of a line fitting may be of any quantity, shape or size, may be constructed of any suitable materials and may be disposed at any suitable locations along the line. The fitting base and projection may be of any quantity, shape or size and may be constructed of any suitable materials. The base channel may be of any shape or size, may be defined in the base at any locations and extend in any desired directions. The fluid line may be secured to the fitting via any conventional or other locks or connectors. The base and projection may be arranged or connected in any fashion, while the fitting may have any suitable configuration (e.g., T-type fitting, Y-type fitting, cross fitting, coupling, etc.). The fitting may be included within and permanently or releasably connected to a disposable IV line set. The temperature probe may be disposed within the fitting projection in any manner via any conventional or other securing mechanisms (e.g., friction fit, adhesives, clamp, threaded engagement, etc.). The fitting may include a receptacle to maintain fluid sterility and permit re-use of the temperature probe. The receptacle may be of any quantity, shape or size, may be constructed of any suitably thermally conductive materials and may be disposed at any locations within the projection or fitting suitable to contact or thermally conduct heat from fluid flowing within the fitting. The receptacle body and flange may be of any quantity, shape or size and may be constructed of any suitable materials. The temperature probe may be secured within the receptacle via any conventional or other securing techniques (e.g., friction fit, threaded engagement, securing mechanism, etc.). Similarly, the receptacle may be secured within the projection or fitting via any conventional or other securing techniques (e.g., friction fit, adhesives, threaded engagement, securing mechanism, etc.).

The securing cap may be of any quantity, shape or size and may be constructed of any suitable materials. The cap channel may be of any shape or size, may be defined at any cap locations and may extend in any desired directions. The temperature probe may be secured within the securing cap via any conventional or other securing techniques (e.g., friction fit, threaded engagement, securing mechanism, etc.). The projection tabs may be of any quantity, shape or size, may be constructed of any desired materials and may be disposed at any locations on the projection or fitting. The channel grooves and notches may be of any quantity, shape or size and may be defined at any locations. The tabs may be secured to the projection or fitting in any manner enabling fracture or removal of the tabs.

The temperature sensing device in the form of an injection fitting may be of any quantity, shape or size, may be constructed of any suitable materials and may be disposed at any suitable locations along the line. The fitting base and inlet portions may be of any quantity, shape or size and may be constructed of any suitable materials. The base and inlet portion channels may be of any shape or size, may be defined in the respective portions at any locations and extend in any desired directions. The fluid line may be secured to the fitting via any conventional or other locks or connectors. The base and inlet portions may be arranged or connected in any fashion, while the fitting may have any suitable configuration (e.g., T-type fitting, Y-type fitting, cross fitting, coupling, etc.). The fitting may be included within and permanently or releasably connected to a disposable IV line set. The temperature probe may include any type of configuration, but is preferably in the form of a syringe, needle or other configuration suitable to penetrate the barrier. The membrane or barrier may be constructed of any suitable nylon or other material. The probe sensing tip and handle may be of any shape or size, and may be disposed at any suitable locations on the probe. The temperature probe may be employed with a sheath or covering to maintain fluid sterility and permit re-use of the probe. The sheath may be of any quantity, shape or size and may be constructed of any suitable thermally conducting materials.

It is to be understood that the present invention is not limited to the specific configurations or applications described above, and may be utilized to determine the temperature of a fluid at any desired location within a fluid line. For example, the temperature sensors or probes may be embedded within, or entirely or partially wrapped about, the fluid line wall to measure and provide fluid temperature to the monitor device. Alternatively, the temperature sensors or probes may be wrapped entirely or partially about a sensing device or holder, or may be disposed within the fluid line (e.g., attached to the fluid line inner diameter). The temperature sensors and probes may be secured to the fluid line or sensing device or holder via any suitable fastening techniques (e.g., snap type fasteners, adhesives, etc.), and may cover any portion of the fluid line and/or sensing device or holder.

The temperature sensing devices described above may be employed with any types of infusion apparatus, such as the apparatus shown in FIG. 2. The temperature sensing devices described above may be placed at any desired locations along a fluid line (e.g., attached to those locations or moved along the fluid line) via any suitable attachment or placement techniques to measure temperature of fluid at those locations. The manners of operation of the temperature sensing devices described above may be modified in any fashion to perform a fluid temperature measurement. A fluid line may include any quantity of temperature sensing devices or corresponding components (e.g., temperature sensors or probes, housings, fittings and/or monitor devices) where temperature measurements may be combined in any fashion (e.g., averaged, weighted, etc.) to determine a fluid temperature.

It is to be understood that the terms "top", "bottom", "front", "rear", "side", "height", "length", "width", "upper", "lower" and the like are used herein merely to describe points of reference and do not limit the present invention to any particular orientation or configuration.

From the foregoing description, it will be appreciated that the invention makes available a novel temperature sensing device for selectively measuring temperature at desired locations along an intravenous fluid line, wherein a temperature sensing device is selectively secured to an intravenous fluid line at any desired location and provides temperature measurements to a monitor device to display the measured fluid temperature to an operator.

Having described preferred embodiments of a new and improved temperature sensing device for selectively measuring temperature at desired locations along an intravenous fluid line, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method of measuring temperature of a fluid at various locations along an intravenous fluid line extending between a fluid source and a patient via a temperature sensing device including a base with a groove defined therein forming a receptacle to receive and retain a portion of said fluid line and to allow said fluid line to extend continuously through said temperature sensing device and a temperature sensor to measure temperature of fluid within said retained fluid line portion, wherein said temperature sensing device further includes a plurality of resilient prongs and said receptacle is disposed on said temperature sensing device between said resilient prongs, said method comprising:

(a) providing a desired location along said fluid line residing at any of a plurality of fluid line locations between said fluid source and said patient from which to measure temperature of said fluid;

(b) receiving said temperature sensing device at a portion of said fluid line corresponding to said desired location, wherein said temperature sensing device is selectively securable to said fluid line at any of said plurality of fluid line locations and said plurality of fluid line locations includes at least one proximal fluid line location toward said fluid source and at least one distal fluid line location toward said patient, and wherein step (b) further includes:

(b.1) receiving said desired fluid line portion between said prongs and within said receptacle formed by said groove within said base; and (b.2) engaging said temperature sensor with said prongs to secure said temperature sensor proximate to said desired fluid line portion;

(c) measuring a temperature of fluid flowing through said selected portion of said fluid line via said temperature sensor; and (d) displaying the measured temperature via a temperature monitor in communication with said temperature sensor.

2. The method of claim 1, wherein each of said prongs includes a transversely extending projection, and step (b.2) further includes:

(b.2.1) engaging said temperature sensor with said projections to retain said temperature sensor between said prongs.

3. The method of claim 1, wherein step (d) further includes:

(d.1) printing said measured temperature via said temperature monitor.

4. The method of claim 1, wherein step (d) further includes:

(d.1) recording measured temperatures of said fluid via said temperature monitor.

5. The method of claim 4, wherein step (d) further includes:

(d.2) printing said recorded measured temperatures via said temperature monitor.

6. A method of measuring temperature of a fluid at various locations along an intravenous fluid line extending between a fluid source and a patient via a temperature sensing device including a receptacle to receive and retain a portion of said fluid line and to allow said fluid line to extend continuously through said temperature sensing device and a temperature sensor to measure temperature of fluid within said retained fluid line portion, wherein said temperature sensor includes a sensing tip disposed within said receptacle, said method comprising:

(a) providing a desired location along said fluid line residing at any of a plurality of fluid line locations between said fluid source and said patient from which to measure temperature of said fluid;

(b) receiving said temperature sensing device at a portion of said fluid line corresponding to said desired location, wherein said temperature sensing device is selectively securable to said fluid line at any of said plurality of fluid line locations and said plurality of fluid line locations includes at least one proximal fluid line location toward said fluid source and at least one distal fluid line location toward said patient, and wherein step (b) further includes:

(b.1) piercing a wall of said desired fluid line portion with said sensing tip;

(c) measuring a temperature of fluid flowing through said selected portion of said fluid line via said temperature sensor, wherein step (c) further includes:

(c.1) directly measuring the temperature of fluid flowing through said desired fluid line portion with said sensing tip; and (d) displaying the measured temperature via a temperature monitor in communication with said temperature sensor.

7. The method of claim 6, wherein said temperature sensing device further includes an upper member pivotally connected to a lower member, each of said upper and lower members includes a groove disposed on an engaging surface, and said grooves of said upper and lower members are aligned on said engaging surfaces to form said receptacle in the form of a channel upon contact between said engaging surfaces, and step (b.1) further includes:

(b.1.1) receiving said desired fluid line portion within said groove on said engaging surface of said lower member; and (b.1.2) pivoting of at least one of said upper and lower members with respect to the other of said upper and lower members to contact said engaging surfaces of said upper and lower members and force said sensing tip to pierce said wall of said desired fluid line portion.

8. The method of claim 7, wherein said engaging surfaces include a locking mechanism, and step (b.1.2) further includes:

(b.1.2.1) locking said upper member against said lower member.

9. The method of claim 6, wherein step (d) further includes:

(d.1) printing said measured temperature via said temperature monitor.

10. The method of claim 6, wherein step (d) further includes:

(d.1) recording measured temperatures of said fluid via said temperature monitor.

11. The method of claim 10, wherein step (d) further includes:

(d.2) printing said recorded measured temperatures via said temperature monitor.

12. A method of measuring temperature of a fluid at various locations along an intravenous fluid line extending between a fluid source and a patient via a temperature sensing device including a receptacle to receive and retain a portion of said fluid line and to allow said fluid line to extend continuously through said temperature sensing device and a temperature sensor to measure temperature of fluid within said retained fluid line portion, wherein said temperature sensing device further includes a resilient member arranged in a spiral configuration with first and second resilient member ends overlapping each other and separated by a gap, said method comprising:

(a) providing a desired location along said fluid line residing at any of a plurality of fluid line locations between said fluid source and said patient from which to measure temperature of said fluid;

(b) receiving said temperature sensing device at a portion of said fluid line corresponding to said desired location, wherein said temperature sensing device is selectively securable to said fluid line at any of said plurality of fluid line locations and said plurality of fluid line locations includes at least one proximal fluid line location toward said fluid source and at least one distal fluid line location toward said patient, and wherein step (b) further includes:

(b.1) receiving said desired fluid line portion within said gap; and (b.2) directing said desired fluid line portion through said gap to be received and secured within said receptacle;

(c) measuring a temperature of fluid flowing through said selected portion of said fluid line via said temperature sensor; and (d) displaying the measured temperature via a temperature monitor in communication with said temperature sensor.

13. The method of claim 12, wherein step (d) further includes:

(d.1) printing said measured temperature via said temperature monitor.

14. The method of claim 12, wherein step (d) further includes:

(d.1) recording measured temperatures of said fluid via said temperature monitor.

15. The method of claim 14, wherein step (d) further includes:

(d.2) printing said recorded measured temperatures via said temperature monitor.

16. A method of measuring temperature of a fluid flowing within an intravenous fluid line at selected locations along said fluid line via a temperature sensing device including a fitting including first and second open ends selectively securable to said fluid line, a passage disposed within said fitting and extending between said first and second open ends to permit fluid flowing within said fluid line to flow through said fitting and a connection port disposed on an exterior surface of said fitting and in fluid communication with said passage, and a temperature sensor to measure temperature of fluid flowing through said fitting, wherein said fitting further includes a receptacle disposed within said connection port and in direct contact with fluid flowing within said passage and said connection port extends from an outer surface of said fitting, said method comprising:

(a) receiving said first and second ends of said fitting at selected portions of said fluid line;

(b) measuring a temperature of fluid flowing through said fitting via said temperature sensor and generating a temperature signal indicating said measured fluid temperature to facilitate electronic display of said measured fluid temperature, wherein step (b) further includes:

(b.1) receiving said temperature sensor within said connection port to contact said receptacle, wherein said temperature sensing device further includes a securing member to secure said temperature sensor to said connection port, said securing member including a recess defined therein with said temperature sensor disposed within said recess, and wherein said securing member and said connection port include a locking mechanism to releasably secure said securing member to said connection port, said locking mechanism including at least one projection removably attached to an outer surface of said connection port and at least one engagement member disposed on said securing member to engage a corresponding projection, and step (b.1) further includes:

(b.1.1) locking said securing member to said connection port by disposing said connection port within said recess to enable said temperature sensor to contact said receptacle; and (b.2) measuring the temperature of said receptacle to indirectly determine the temperature of fluid flowing within said fitting;

(c) electronically displaying the temperature measured by said temperature sensor via a display device; and (d) removing said at least one projection from said connection port via said corresponding engagement member in response to disengagement of said securing member with said connection port to thereby prevent re-engagement of said connection port with said securing member and re-use of said fitting.

\* \* \* \* \*